United States Patent [19]

Cauwenberg et al.

[11] Patent Number: 6,133,450
[45] Date of Patent: Oct. 17, 2000

[54] PROCESS FOR RECOVERY OF PYRIDINE-2, 3-DICARBOXYLIC ACID

[75] Inventors: Veerle Cauwenberg, Leuven, Belgium; Peter J. D. Maas, Schinnen; Franciscus H. P. Vergossen, Echt, both of Netherlands

[73] Assignee: DSM N.V., Heerlen, Netherlands

[21] Appl. No.: 09/283,757

[22] Filed: Apr. 2, 1999

[30] Foreign Application Priority Data

Apr. 2, 1998 [NL] Netherlands .............. 1008788

[51] Int. Cl.$^7$ .............................. C07D 213/30
[52] U.S. Cl. .............................. 546/321
[58] Field of Search .............................. 546/321

[56] References Cited

U.S. PATENT DOCUMENTS 4,537,971  8/1985  Rebhahn et al. .............. 546/320
5,635,071  6/1997  Al-Samadi .............. 210/652

FOREIGN PATENT DOCUMENTS 0 780 152 A1  6/1997  European Pat. Off. .

*Primary Examiner*—Jane Fan
*Attorney, Agent, or Firm*—Pillsbury Madison & Sutro LLP

[57] ABSTRACT

Process for recovering a pyridine-2,3-dicarboxylic acid from a process stream in the preparation process of the pyridine-2,3-dicarboxylic acid in which the process stream is subjected to nanofiltration at a pH higher than 4.5 and the pyridine-2,3-dicarboxylic acid-containing concentrate is utilised. Preferably, the pH is chosen to be between 7 and 9 and the concentration factor in nanofiltration greater than 3.

In a suitable embodiment the process stream is formed by the mother liquor obtained in the preparation of pyridine-2, 3-dicarboxylic acid by oxidising a suitable quinoline or the corresponding 2,3-lutidine and separating the solid material.

13 Claims, 1 Drawing Sheet

1

PROCESS FOR RECOVERY OF PYRIDINE-2, 3-DICARBOXYLIC ACID

FIELD OF THE INVENTION

The invention relates to a process for recovering a pyridine-2,3-dicarboxylic acid from a process stream in the preparation process of the pyridine-2,3-dicarboxylic acid.

BACKGROUND OF THE INVENTION

Pyridine-2,3-dicarboxylic acids are used as for example a raw material in the preparation of pharmaceuticals, agrochemicals and colorants. Pyridine-2,3-dicarboxylic acids can be prepared by various known processes. In these processes the product obtained usually is isolated by acidifying the reaction mixture and then crystallising and isolating it. The remaining mother liquor, which usually contains not only salts and by-products but also substantial amounts of pyridine-2,3-dicarboxylic acid, is difficult to work up. Recirculation causes an undesired accumulation of by-products, necessitating a relatively large blow-down with associated losses of pyridine-2,3-dicarboxylic acid. Furthermore, the stream is highly dilute.

SUMMARY AND OBJECTS OF THE INVENTION

The invention provides a process for recovery of pyridine-2,3-dicarboxylic acids from a process stream in which process there is obtained a concentrated stream which contains virtually all pyridine-2,3-dicarboxylic acid and which, in addition, contains practically no by-products and salts. This is achieved according to the process by subjecting the process stream to nanofiltration at a pH higher than 4.5.

Surprisingly, it has been found that pyridine-2,3-dicarboxylic acid exhibits high retention in nanofiltration whilst the by-products, which often are highly similar in terms of molecular structure and molecular weight, as well as salts, exhibit low retention.

DETAILED DESCRIPTION OF THE INVENTION

Figure 1:
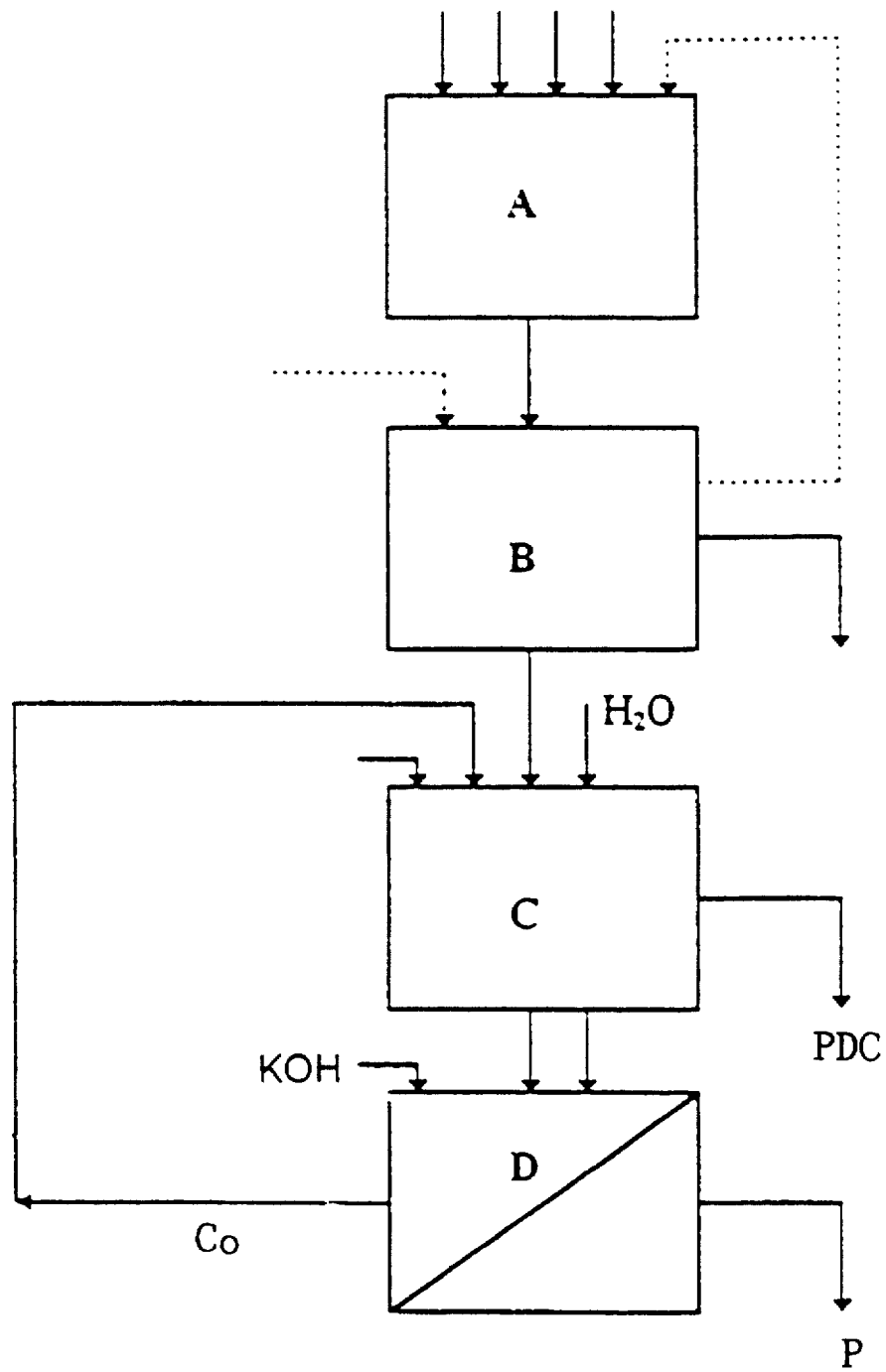
FIG. 1 depicts the process including the oxidation, purification recovery in nanofiltration steps.

The present process involves recovering a pyridine-2,3-dicarboxlyic acid from a process stream in the preparation process of the pyridine-2,3-dicarboxlyic acid, wherein the process stream is subjected to nanofiltration at a pH greater than 4.5 and the pyridine-2,3-dicarboxylic acid-containing concentrate is utilized.

In the context of the present invention, nanofiltration means a pressure-driven membrane process in which the membrane possesses high retention for components having a molecular weight of about 100D and higher and low retention for monovalent salts (+20 to –40%). It is preferred for operation to take place at a feed pressure which is higher than atmospheric and preferably is between 1 and 5 MPa. The permeate flux increases with increasing pressure.

The retention of a component i ($R_i$) expressed in per cent is defined by the formula $R_i=(1-C_{ip}/C_{if})\times 100\%$ where $C_{ip}$ is the concentration of component i in the permeate and $C_{if}$ is the concentration of component i in the feed, both expressed in % wt.

Pyridine-2,3-dicarboxylic acids can be prepared by for example oxidising quinoline (derivatives) and pyridinedivinyl derivatives as described in for example U.S. Pat. No. 4,537,971 and in the non-prepublished Belgian patent application No. 9601046, by electrochemical oxidation of 2,3-lutidine or by oxidation of 2,3-lutidine with the aid of a suitable oxidiser or with the aid of a suitable catalyst/solvent system. Other methods of preparation are for example hydrolysis of 2,3-pyridinedinitriles, 2,3-pyridinediesters or 2,3-pyridinediamides or carbonylation of 2,3-pyridinedihalo compounds or 2,3-pyridineditriflate compounds. In practice, unconverted starting products often remain behind in all of these methods and in addition other by-products are formed that are difficult to separate from the pyridine-2,3-dicarboxylic acid and remain behind in the mother liquor after recovery of the pyridine-2,3-dicarboxylic acid. The process streams from which the pyridine-2,3-dicarboxylic acid is recovered usually are aqueous or alcoholic process streams.

Preferably, a concentration factor higher than 3 is achieved in the nanofiltration. This is because the retention factor for the pyridine-2,3-dicarboxylic acid has been found to remain high at higher concentration factors whilst the retention factors for by-products decreases at higher concentration factors. By the concentration factor achieved at any time during nanofiltration is meant the ratio of the process stream initially to be filtered to the process stream to be filtered at that particular time.

The pH at which the nanofiltration is carried out is higher than 4.5. Preferably, the nanofiltration is carried out at a high pH because a higher retention of the pyridine-2,3-dicarboxylic acid and better separation of the pyridine-2,3-dicarboxylic acid and the by-products can be achieved at higher pH values. Preferably, the pH is not chosen to be extremely high because the stability of the various components, for example the membranes and the pyridine-2,3-dicarboxylic acid, decreases at extremely high pH. Consequently, the pH is preferably chosen between 5.5 and 10, in particular between 7 and 9.

The process of the invention may in principle employ any type of nanofiltration module. Suitable modules that may be employed are for example tubular, capillary, hollow fibre, flat plates, spiral-wound and disc-type modules. It is preferred for tubular, capillary or spiral-wound modules to be used.

The type of membrane to be used is not critical either. Suitable membranes that may be employed are for example organic (polymeric), organomineral and inorganic membranes.

Polymeric membranes for nanofiltration include membranes based on polysulphone, polyethersulphone, polyacrylonitrile, cellulose ester, polyimide/polyetherimide, polyamide, polyvinylidenefluoride and composite membranes.

Organomineral membranes consist of a polymeric support, for example polysulphone, to which inorganic precipitates, for example oxides (Si oxide, Zr oxide or mixtures of oxides) are added.

Examples of inorganic membranes are ceramic membranes, glass-like membranes and metallic membranes; for the present application especially ceramic membranes. Ceramic membranes are formed by a combination of a metal, for example aluminium, titanium or zirconium, with a non-metal in the form of an oxide, nitride or carbide. Such membranes currently are in the development phase.

Preferably, use is made of composite membranes containing a selective top layer which substantially is negatively charged and which is applied to an ultrafiltration membrane serving as a support layer.

Such membranes are commercially available. Suitable membranes in the context of the invention are for example of the SelRo®-type (from Kiryat Weizmann Ltd.), DRC-1000® (from Celfa), NF-PES-10/PP60® (from Kalle), NTR 7410® (from Nitto) and WFN 0505® (from Stork Friesland).

The temperature at which the nanofiltration is carried out is not particularly critical. To prevent membrane damage, it is undesirable for the nanofiltration to take place at a temperature at which the process stream may freeze. Preferably, a temperature is chosen between 0 and 80° C. depending on the membrane selected. Ambient temperature is particularly suitable. At higher temperatures, because of favourable viscosity of the streams, however, a higher flux is achieved, which may also be advantageous.

As a rule, the permeate streams obtained in the process, which contain strongly reduced concentrations of raw materials in comparison with the treated process streams, need not be subjected to a second treatment according to the invention. The retentate streams obtained may, dependent on the quality thereof, be directly returned to the preparation process or separately be worked up to endproduct.

After being used—or if the permeability of the membranes decreases—the membranes can easily be cleaned, at somewhat increased temperature if desired, by rinsing with (demi)water and/or a caustic solution, and/or by rinsing in the presence of a small amount of a compound having rinsing activity, for example Ultrasil® or ethylenediaminetetraacetic acid (EDTA). Increasing the pressure leads to an increase in the retention value for the raw materials. According as the concentration factor is chosen to be higher (by adjustment of the process conditions), larger amounts, in absolute terms, of the raw materials will usually be discharged via the permeate, as a result of which the amount of raw material in the retentate to be recovered will be smaller.

The process of the invention can be carried out both batch-wise and continuously.

The invention will now be illustrated by a number of examples without being limited thereto.

EXAMPLE

Pyridine-2,3-dicarboxylic acid was prepared by oxidising 2,3-lutidine. The reaction mixture was purified. Subsequently, pyridine-2,3-dicarboxylic acid was crystallised at pH=1, centrifuged, washed and dried. The remaining combined stream of mother liquor and washing water had a pH value of 1 and contained 1.0 % wt. pyridine-2,3-dicarboxylic acid, 0.015 % wt. picolinic acid, 0.13 % wt. 3-methylpicolinic acid, 0.04% wt. nicotinic acid, 0.54 % wt. 2-methylnicotinic acid and about 20 % wt. KCl. The combined stream of mother liquor and washing water was alkalised to pH=8.5 with a 25% aqueous KOH solution. This stream was fed to a nanofiltration unit having type WFN0505 tubular composite membranes from Stork Friesland. Nanofiltration was carried out at 40° C. and a pressure of 3 MPa in a PCI Microlab 80 membrane unit with two tubular membranes having a membrane area of 0.15 m$^2$.

The feed was concentrated to a concentration factor of 6. The permeate (P) was discharged and did not require any further purifying; the concentrate (Co) was recirculated to the crystallisation step. In this way, 83% of the pyridine-2, 3-dicarboxylic acid (PDC) present was recovered. The recirculation stream had no effect on the product quality. Blowdown was not necessary because the by-products did not accumulate. This is also apparent from the retention values for the various components summarized in Table 1.

The process is elucidated in FIG. 1: A is the oxidation step; B is the purification step; C is the recovery of pyridine-2,3-dicarboxylic acid and D is the nanofiltration step.

TABLE I

Retention values for the various components

| Component | Local retention[1] at beginning of concentration (%) | Local retention[1] at end of concentration (%) |
| --- | --- | --- |
| pyridine-2,3-dicarboxylic acid | 91.6 | 85.6 |
| picolinic acid | 16.9 | −29.8 |
| 3-methylpicolinic acid | 35.9 | −16.1 |
| nicotinic acid | 8.0 | −20.8 |
| 2-methylnicotinic acid | 23.4 | −18.6 |
| Cl⁻ | −30.0 | −35.3 |

[1]Local retention $R_i$ is defined as $R_i = 1 - C_{ip} / C_{ir}$ where $C_{ip}$ and $C_{ir}$ are the concentrations in the permeate and the retentate, respectively.

What is claimed is:

1. A process for recovering a pyridine-2,3-dicarboxylic acid from a process stream in the preparation process of the pyridine-2,3-dicarboxylic acid in which process the process stream is subjected to nanofiltration at a pH higher than 4.5 wherein in said nanofiltration the feed pressure is higher than atmospheric pressure, and the pyridine-2,3-dicarboxylic acid-containing concentrate is utilized.

2. A process according to claim 1, wherein the pH is between 7 and 9.

3. A process according to claim 1 or 2, wherein the concentration factor in nanofiltration is greater than 3.

4. A process according to claim 1 or 2, wherein the process stream is formed by the mother liquor obtained in the preparation of the pyridine-2,3-dicarboxylic acid by oxidizing a quinoline and separating the solid material.

5. A process according to claim 1 or 2, wherein the process stream is formed by the mother liquor obtained in the preparation of the pyridine-2,3-dicarboxylic acid by oxidizing the corresponding 2,3-lutidine and separating the solid material.

6. A process for the preparation of a pyridine-2,3-dicarboxylic acid in which a suitable quinoline is subjected to an oxidation and in which the pyridine-2,3-dicarboxylic acid is subsequently recovered from the reaction mixture, wherein the mother liquor that remains after the recovery of the pyridine-2,3-dicarboxylic acid is subjected to a process according to claim 4.

7. A process for preparing a pyridine-2,3-dicarboxylic acid in which a corresponding, 2,3-lutidine is subjected to an oxidation and the pyridine-2,3-dicarboxylic acid is subsequently recovered from the reaction mixture, wherein the mother liquor that remains after the recovery of the pyridine-2,3-dicarboxylic acid is subjected to a process according to claim 4.

8. A process according to claim 1, wherein the nanofiltration is conducted at a temperature in the range of 0° C. to 80° C.

9. A process according to claim 1, wherein said nanofiltration the feed pressure is between 1 Mpa and 5 Mpa.

10. A process according to claim 4, wherein said nanofiltration is conducted at a temperature between 0° C. and 80° C., a feed pressure during said nanofiltration of between 1 Mpa and 5 Mpa, and a pH which is between 7 and 9.

11. A process according to claim 5, wherein said nanofiltration is conducted at a temperature between 0° C. and 80° C., a feed pressure during said nanofiltration of between 1 Mpa and 5 Mpa, and a pH which is between 7 and 9.

12. A process according to claim 3, wherein the process stream is formed by the mother liquor obtained in the preparation of the pyridine-2,3-dicarboxylic acid by oxidizing a quinoline and separating the solid material.

13. A process according to claim 3, wherein the process stream is formed by the mother liquor obtained in the preparation of the pyridine-2,3-dicarboxylic acid by oxidizing the corresponding 2,3-lutidine and separating the solid material.

* * * * *